(12) United States Patent
Nakamura et al.

(10) Patent No.: US 7,275,538 B2
(45) Date of Patent: Oct. 2, 2007

(54) INHALING TYPE MEDICINE ADMINISTERING APPARATUS AND MEDICINE CARTRIDGE USED THEREIN

(75) Inventors: Shigemi Nakamura, Gunma (JP); Hisatomo Ohki, Gunma (JP); Kazunori Ishizeki, Gunma (JP); Akira Yanagawa, Yokohama (JP)

(73) Assignees: Hitachi, Ltd., Kanagawa (JP); Dott Limited Company, Tokyo (JP)

( * ) Notice: Subject to any disclaimer, the term of this patent is extended or adjusted under 35 U.S.C. 154(b) by 0 days.

(21) Appl. No.: 11/217,328

(22) Filed: Sep. 2, 2005

(65) Prior Publication Data

US 2006/0096595 A1 May 11, 2006

(30) Foreign Application Priority Data

Nov. 8, 2004 (JP) ............................. 2004-323910

(51) Int. Cl.
*A61M 15/00* (2006.01)
(52) U.S. Cl. ............................. 128/203.15; 128/203.19
(58) Field of Classification Search ........... 128/203.15, 128/203.19, 203.21
See application file for complete search history.

(56) References Cited

U.S. PATENT DOCUMENTS

| | | | | |
|---|---|---|---|---|
| 4,627,432 A * | 12/1986 | Newell et al. | ......... | 128/203.15 |
| 5,035,237 A * | 7/1991 | Newell et al. | ......... | 128/203.15 |
| 5,207,217 A * | 5/1993 | Cocozza et al. | ....... | 128/203.21 |
| 5,415,162 A | 5/1995 | Casper et al. | | |
| 5,492,112 A * | 2/1996 | Mecikalski et al. | ..... | 128/203.15 |
| 5,642,727 A * | 7/1997 | Datta et al. | ............ | 128/203.15 |
| 5,647,349 A * | 7/1997 | Ohki et al. | ............ | 128/203.15 |
| 5,660,169 A * | 8/1997 | Kallstrand et al. | ..... | 128/203.15 |
| 5,715,811 A * | 2/1998 | Ohki et al. | ............ | 128/203.21 |
| 5,752,505 A * | 5/1998 | Ohki et al. | ............ | 128/203.15 |
| 5,996,577 A * | 12/1999 | Ohki et al. | ............ | 128/203.15 |
| 6,029,663 A * | 2/2000 | Eisele et al. | ........... | 128/203.21 |
| 6,065,472 A * | 5/2000 | Anderson et al. | ...... | 128/203.21 |
| 6,273,086 B1 * | 8/2001 | Ohki et al. | ............ | 128/203.21 |
| 6,328,034 B1 * | 12/2001 | Eisele et al. | ........... | 128/203.15 |
| 6,341,605 B1 * | 1/2002 | Ohki et al. | ............ | 128/203.15 |
| 6,371,111 B1 * | 4/2002 | Ohki et al. | ............ | 128/203.15 |
| 6,626,173 B2 * | 9/2003 | Genova et al. | ........ | 128/203.15 |
| 6,722,364 B2 * | 4/2004 | Connelly et al. | ...... | 128/203.15 |
| 6,810,872 B1 * | 11/2004 | Ohki et al. | ............ | 128/203.15 |
| 6,948,492 B2 * | 9/2005 | Wermeling et al. | .... | 128/200.14 |
| 2005/0172963 A1 * | 8/2005 | Allan et al. | ............ | 128/203.15 |

FOREIGN PATENT DOCUMENTS

| | | |
|---|---|---|
| EP | 0 547 429 A1 | 6/1993 |
| JP | 2002-535048 A | 10/2002 |
| WO | WO95/031238 A1 | 11/1995 |
| WO | WO98/004308 A1 | 2/1998 |
| WO | WO 03/024514 A1 | 3/2003 |
| WO | WO 03/066470 A1 | 8/2003 |

* cited by examiner

*Primary Examiner*—Steven O. Douglas
(74) *Attorney, Agent, or Firm*—Sughrue Mion, PLLC

(57) ABSTRACT

A medicine cartridge including a medicine accommodating body having a plurality of medicine accommodating sections formed side by side with each other in a peripheral direction of the medicine accommodating body. Each medicine accommodating section accommodates therein medicine in powder form. A section defining an inflow hole is formed at the inner peripheral side of the medicine accommodating body to supply air into the medicine accommodating section. A section defining an outflow hole is formed at the outer peripheral side of the medicine accommodating body to flow out the medicine introduced by air.

3 Claims, 4 Drawing Sheets

INHALING TYPE MEDICINE ADMINISTERING APPARATUS AND MEDICINE CARTRIDGE USED THEREIN

BACKGROUND OF THE INVENTION

This invention relates to improvements in an inhaling type medicine administering apparatus for administering powdered medicine upon suction, and a medicine cartridge used in the medicine administering apparatus.

Hitherto, various types of the inhaling type medicine administering apparatuses are proposed and put into practical use, for example, for bronchodilation treatment in which powdered medicine is administered upon suction by the patient. One of such medicine administering apparatuses is disclosed in a Japanese Patent Provisional Publication No. 2002-535048, in which the medicine administering apparatus includes a disk formed with a plurality of cavities for accommodating medicine. Upon rotating the disk, a plurality of times of medicine administering can be carried out. Each cavity for accommodating medicine is formed extending in the direction of the thickness of the disk. The front surface side of each cavity for accommodating medicine is sealed with a sealing tape which is adhered to the front surface side of each cavity and formed into a spiral shape.

SUMMARY OF THE INVENTION

However, with the above medicine administering apparatus of the conventional technique, each cavity for accommodating medicine is opened only at the front surface of the disk so that the medicine filled in the cavity for accommodating medicine has to be sucked up by the patient. As a result, in case that the patient is a child or the like who is weak in suction force, it is difficult to sufficiently suck up medicine from the cavity for accommodating medicine so that there arises a problem that the medicine avoidably remains within the cavity for accommodating medicine.

Additionally, the above conventional medicine administering apparatus is operated by peeling off the sealing tape from the front surface side of the cavity at every administering operation. Consequently, the above conventional medicine administering apparatus needs a mechanism for rolling up the peeled sealing tape, and therefore the configuration of the medicine administering apparatus tends to be complicated. As a result, the whole body of the medicine administering apparatus becomes large in size thereby causing cost to be increased.

It is an object of the present invention is to provide an improved inhaling type medicine administering apparatus and an improved medicine cartridge which can effectively overcome drawbacks encountered in conventional inhaling type medicine administering apparatuses.

Another object of the present invention is to provide an improved inhaling type medicine administering apparatus and an improved medicine cartridge by which even a patient who is weak in suction force can sufficiently inhale medicine without remaining medicine within a medicine accommodating cavity, with a simplified configuration of the medicine administering apparatus and the medicine cartridge.

An aspect of the present invention resides in a medicine cartridge which comprises a medicine accommodating body including a plurality of medicine accommodating sections formed side by side with each other in a peripheral direction of the medicine accommodating body. Each medicine accommodating section accommodates therein medicine in powder form. A section defining an inflow hole is formed at the inner peripheral side of the medicine accommodating body to supply air into the medicine accommodating section. A section defining an outflow hole is formed at the outer peripheral side of the medicine accommodating body to flow out the medicine introduced by air.

With the above arrangement, the medicine accommodating body is provided at its outer peripheral side with the outflow hole through which the medicine is flowed out under the influence of the air. The medicine accommodating section, the inflow hole, and the outflow hole are arranged along the periphery of the medicine accommodating body so as to effectively dispose medicines for a plurality of doses.

Another aspect of the present invention resides in an inhaling type medicine administering apparatus which comprises a medicine cartridge. A cartridge accommodating section is provided for detachably accommodating the medicine cartridge. A section defining an inflow passage through which air is supplied into the medicine accommodating section of the medicine cartridge is provided. A suction mouth through which the medicine in the medicine accommodating section is drawn out with air supplied from the inflow passage and administered into lungs of a person is provided. The medicine cartridge includes a medicine accommodating body having a plurality of medicine accommodating sections formed side by side with each other in a peripheral direction of the medicine accommodating body. Each medicine accommodating section accommodates therein medicine in powder form. A section defining an inflow hole is formed at the inner peripheral side of the medicine accommodating body to supply air into the medicine accommodating section. A section defining an outflow hole is formed at the outer peripheral side of the medicine accommodating body to flow out the medicine introduced by air.

With the above arrangement, the medicine accommodating section of the medicine cartridge is provided at its inner peripheral side with the inflow hole for supplying air into the medicine accommodating section, and at its outer peripheral side with the outflow hole for flowing out the medicine drawn out by the air. As a result, it becomes possible to effectively dispose medicines for a plurality of doses, and additionally to simplify the configuration of the inhaling type medicine administering apparatus.

A further aspect of the present invention resides in an inhaling type medicine administering apparatus which comprises a medicine cartridge. A cartridge accommodating section is provided for detachably accommodating the medicine cartridge. A section defining an inflow passage through which air is supplied into the medicine accommodating section of the medicine cartridge is provided. A suction mouth through which the medicine in the medicine accommodating section is drawn out with air supplied from the inflow passage and administered into lungs of a person is provided. The medicine cartridge includes a medicine accommodating body having a plurality of medicine accommodating sections formed side by side with each other in a peripheral direction of the medicine accommodating body. Each medicine accommodating section accommodates therein medicine in powder form. A section defining an inflow hole is formed at the inner peripheral side of the medicine accommodating body to supply air into the medicine accommodating section. A section defining an outflow hole is formed at the outer peripheral side of the medicine accommodating body to flow out the medicine introduced by air. The medicine accommodating body is formed annular.

The suction mouth is bought into communication with each of the medicine accommodating sections by rotating the medicine cartridge.

With the above arrangement, the suction mouth and the medicine accommodating section can be brought into communication with each other by rotating the medicine cartridge, so that it become possible to readily accomplish a plurality of medicine administering operations.

The other objects and features of this invention will become understood from the following description with reference to the accompanying drawing.

BRIEF DESCRIPTION OF THE DRAWINGS

In the drawings, like reference numerals designate like parts and elements throughout all figures in which.

DETAILED DESCRIPTION OF THE INVENTION

Referring now to FIGS. 1 to 6, an embodiment of an inhaling type medicine administering apparatus including a medicine cartridge, according to the present invention is illustrated.

Figure 1:
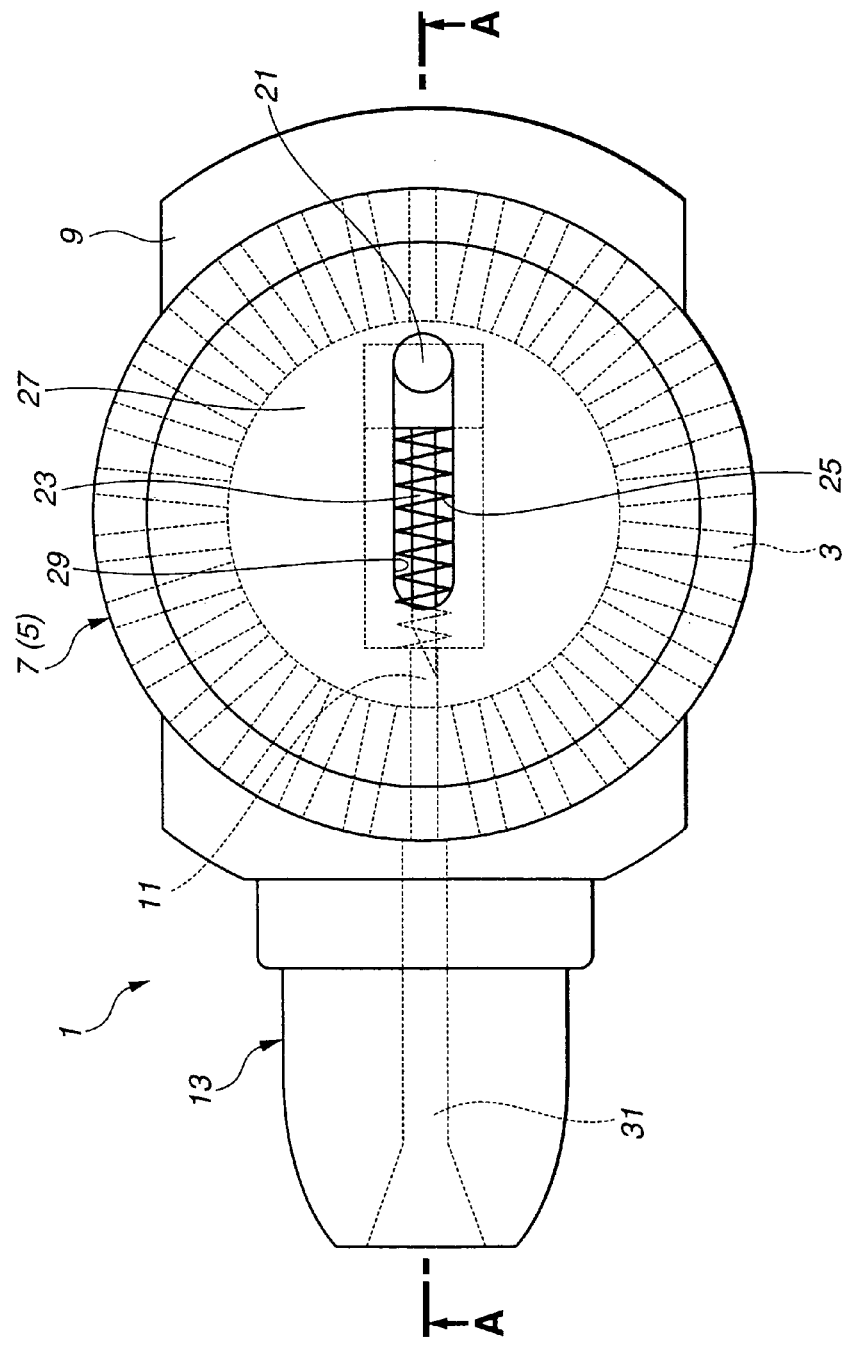
FIG. 1 is a plan view of an embodiment of an inhaling type medicine administering apparatus according to the present invention.
Figure 2:
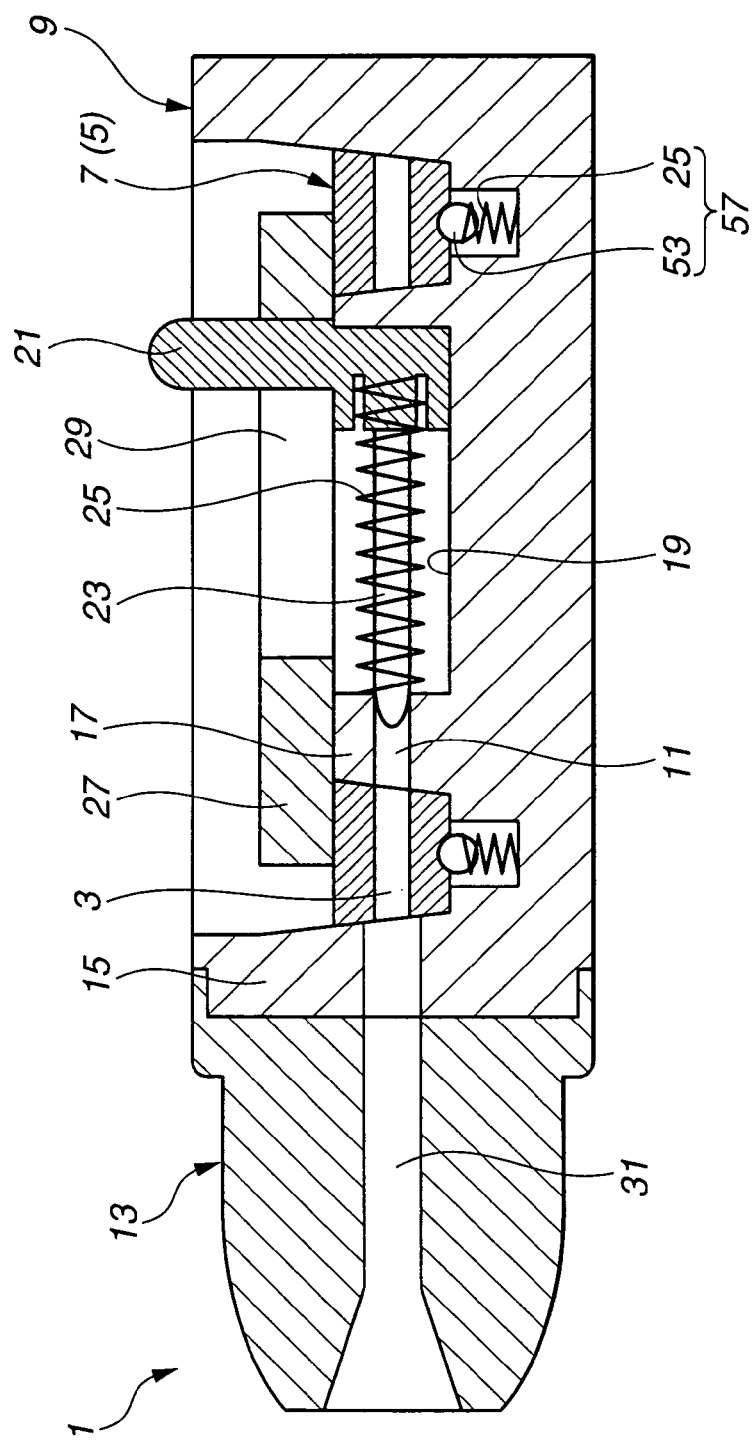
FIG. 2 is a cross-sectional view taken in the direction of the arrows substantially along the line A-A of FIG. 1.

FIG. 1 is a plan view of an embodiment of an inhaling type medicine administering apparatus according to the present invention. FIG. 2 is a cross-sectional view taken in the direction of the arrows substantially along the line A-A of FIG. 1. As shown in FIGS. 1 and 2, inhaling type medicine administering apparatus 1 includes medicine cartridge 7 having medicine accommodating body 5 in which a plurality of medicine accommodating sections 3 for accommodating powdered medicine are formed side by side with each other in a peripheral direction of medicine cartridge 7. Medicine cartridge 7 is detachably accommodated in cartridge accommodating section 9. Air is supplied through inflow passage 11 to the inside of medicine accommodating section 3 in medicine cartridge 7. The medicine within medicine accommodating section 3 is sucked from medicine accommodating section 3 under the influence of airflow supplied through inflow passage 11, and then this sucked medicine is administered into lungs of a patient through suction mouth 13.

Cartridge accommodating section 9 includes outer periphery supporting section 15 which supports an outer peripheral side of medicine cartridge 7, and inner periphery supporting section 17 which supports an inner peripheral side of medicine cartridge 7. Depression section 19 for accommodating perforating pin 23 serves as a pin accommodating section and is formed to extend along a longitudinal direction of inhaling type medicine administering apparatus 1. Operating lever 21 is disposed in depression section 19 (or the pin accommodating section) for accommodating perforating pin, in a manner to be slidably supported. Operating lever 21 is provided at its lower end section with perforating pin 23. Spring 25 is mounted on the outer peripheral surface of perforating pin 23. A tip end section of perforating pin 23 is accommodated within inflow passage 11 which is formed piercing inner periphery supporting section 17.

Disc-like supporting plate 27 is disposed on the upper surface of medicine cartridge 7 to pressingly hold the upper surface of medicine cartridge 7. Supporting plate 27 is formed with elongation hole 29 extending in the longitudinal direction of inhaling type medicine administering apparatus 1. Above operating lever 21 is slidably supported in this elongation hole 29.

Above suction mouth 13 is fixed with cartridge accommodating section 9 thereby forming medicine passage 31 along the longitudinal direction of inhaling type medicine administering apparatus 1.

Additionally, medicine accommodating section 3 is formed generally cylindrical.

Figure 3:
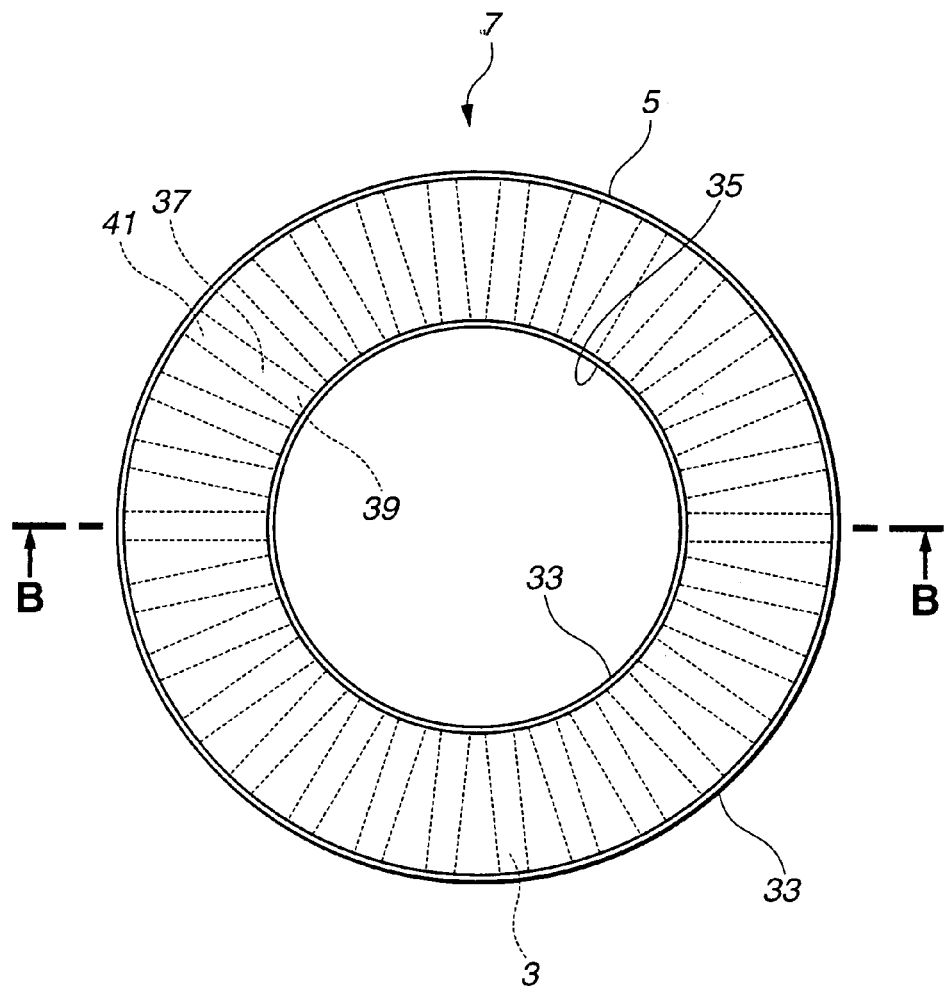
FIG. 3 is a plan view of a medicine cartridge used in the medicine administering apparatus of FIG. 1.
Figure 4:
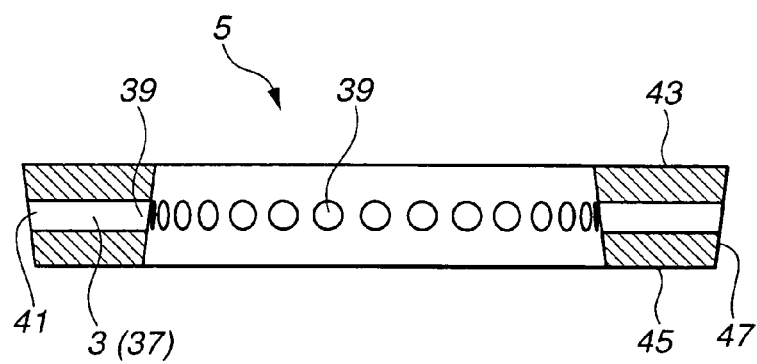
FIG. 4 is a cross-sectional view taken in the direction of the arrows substantially along the line B-B of FIG. 3, showing a medicine accommodating body in a state where sealing tapes are omitted.

FIG. 3 is a plan view of a medicine cartridge used in the medicine administering apparatus of FIG. 1. FIG. 4 is a cross-sectional view taken in the direction of the arrows substantially along the line B-B of FIG. 3, showing a medicine accommodating body in a state where sealing tapes are omitted.

As shown in FIG. 3, medicine cartridge 7 includes medicine accommodating body 5 in which a plurality of medicine accommodating sections 3 are formed side by side with each other in a peripheral direction of medicine cartridge 7. Sealing tapes 33, 33 are respectively put on the inner peripheral side and the outer peripheral side of medicine accommodating body 5. Medicine accommodating section 3 of medicine accommodating body 5 is filled with powdered medicine (not shown).

Above medicine accommodating body 5 is formed at its central section with circular installation opening 35. Medicine accommodating body 5 is formed generally in an annular shape.

As shown in FIGS. 3 and 4, introduction passage 37 is located at the middle section in a thickness direction of medicine accommodating body 5 and formed to pierce medicine accommodating body 5 in a direction of from an inner peripheral side to an outer peripheral side. Introduction passage 37 is formed generally cylindrical and is straight extended in a radial direction of medicine accommodating body 5. Introduction passage 37 has inflow hole 39 located at its one end or inner peripheral side, air being supplied to the inside of medicine accommodating section 3 through inflow hole 39. Additionally, introduction passage 37 has outflow hole 41 located at its other end or outer peripheral side, the medicine sucked under the influence of airflow introduced through inflow passage 39 being flown out through outflow hole 41. Thus, the one end of introduction passage 37 defines inflow hole 39, while the other end of introduction passage 37 defines outflow hole 41 so that inflow hole 39 and outflow hole 41 are respectively arranged on opposite sides in each introduction passage 37. Regarding each medicine accommodating section 3, introduction passage 37, inflow hole 39, and outflow hole 41 are arranged on the same straight line.

Sealing tapes (tape-like members) 33, 33 are put respectively on the inner peripheral surface and the outer peripheral surface of medicine accommodating body 5 so that inflow hole 39 and outflow hole 41 are respectively sealed by these sealing tapes 33, 33. Thus, medicine accommodating section 3 is filled with powdered medicine and sealed by sealing tapes 33, 33.

As shown in FIG. 4, medicine accommodating body 5 is formed in a trapezoid shape in cross-section such that the diametrical length of upper surface 43 is longer than that of lower surface 45. That is to say, medicine accommodating body 5 is formed in such the trapezoid shape (in cross-section) that the length of the lower side corresponding to lower surface 45 is shorter than the length of the upper side corresponding to upper surface 43 and opposite to the lower side. Consequently, in FIG. 4, side surface 47 is tapered to gradually decrease in diameter in a direction of from upper surface 43 to lower surface 45.

Figure 5:
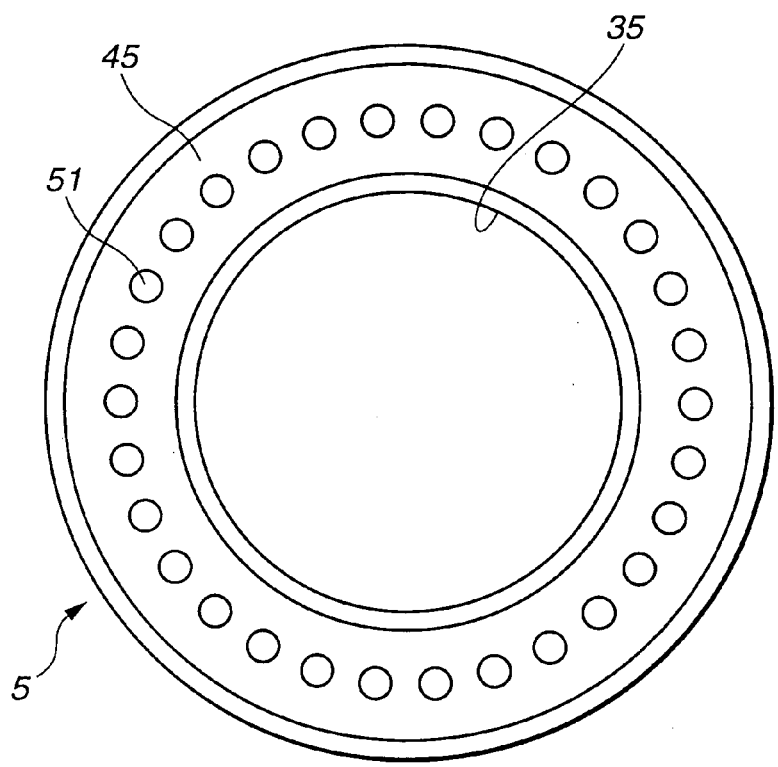
FIG. 5 is a bottom view of the medicine accommodating body of FIG. 4.

FIG. 5 is a bottom view of medicine accommodating body of FIG. 4. Lower surface 45 of medicine accommodating body 5 is formed with a plurality of hemispherical depressions 51 arranged in the periphery of the lower surface 45 at certain intervals. Additionally, cartridge accommodating section 9 is provided with supporting means 57 which includes spherical supporting member 53 and spring 25 so that spherical supporting member 53 is pushed upward by spring 25. As a result, the position of medicine accommodating body 5 in peripheral direction is securely kept upon fitting of spherical supporting member 53 with hemispherical depression 51 of medicine cartridge 7.

Figure 6:
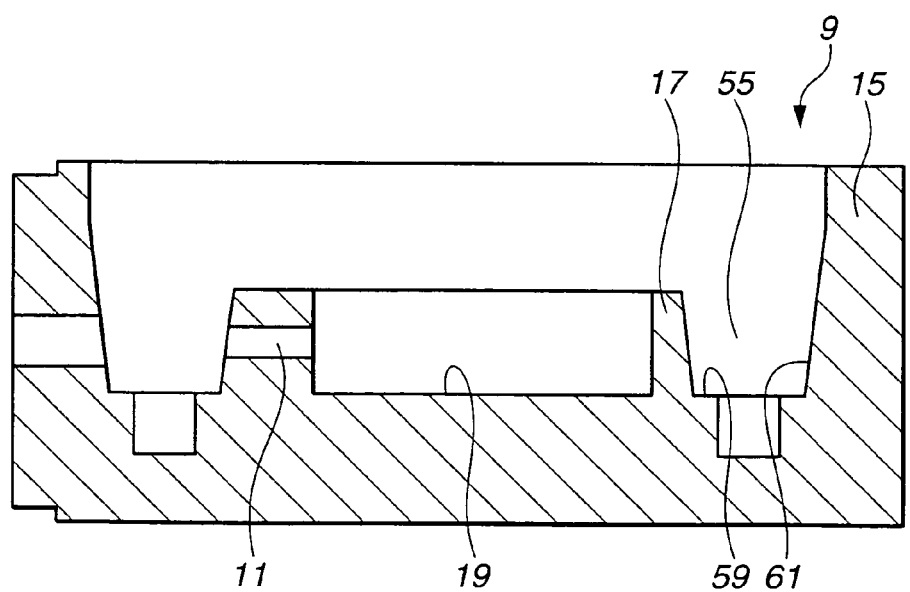
FIG. 6 is a cross-sectional view of a cartridge accommodating section of the medicine administering apparatus of FIG. 2.

FIG. 6 is a cross-sectional view of a cartridge accommodating section of the medicine administering apparatus of FIG. 2. As discussed above, cartridge accommodating section 9 includes outer periphery supporting section 15 for supporting the outer peripheral side of medicine cartridge 7, inner periphery supporting section 17 for supporting the inner peripheral side of medicine cartridge 7, and depression section 19 for accommodating perforating pin. Cartridge fitting section 55 having a cross-sectional shape corresponding to the cross-section of medicine cartridge 7 is formed between inner periphery supporting section 17 and outer periphery supporting section 15 so that medicine cartridge 7 is fitted to cartridge fitting section 55 to be accommodated and retained. Cartridge fitting section 55 is formed as a depression corresponding to medicine cartridge 7 in cross-sectional shape. More specifically, the cartridge fitting section 55 includes bottom wall 59 with which lower surface 45 of medicine cartridge 7 or medicine accommodating body 5 is brought into contact, and side wall 61 with which side surface 47 of medicine cartridge 7 or medicine accommodating body 5 is brought into contact, so that medicine cartridge 7 can be accommodated in cartridge fitting section 55 without clearance.

Above medicine cartridge 7 or medicine accommodating body 5 is formed annular formed with installation opening 35 located on its inner peripheral side. In case that medicine cartridge 7 is installed to cartridge fitting section 55, the inner peripheral surface of medicine cartridge 7 is in contact with side wall 61 of inner periphery supporting section 17 of cartridge accommodating section 9, so that medicine cartridge 7 can be securely supported in position.

Hereinafter, brief discussion will be made on operational procedure of inhaling type medicine administering apparatus according to this embodiment.

First, the patient grasps cartridge accommodating section 9 of inhaling type medicine administering apparatus 1, and then rotates medicine cartridge 7 in peripheral direction so as to locate medicine cartridge 7 at a position where unused medicine accommodating section 3 faces perforating pin 23. Thereafter, operating lever 21 is slid toward the side of suction mouth 13. By this, perforating pin 23 pierces sealing tape 33 at the inner peripheral side, medicine accommodating section 3, and sealing tape 33 at the outer peripheral side.

Subsequently, the patient puts suction mouth 13 in an oral cavity and take breath. By this, air flows through inflow passage 11 into medicine accommodating section 3 so that the medicine filled in medicine accommodating section 3 flows through medicine passage 31 of suction mouth 13 into the oral cavity of the patient, and then smoothly sucked into lungs of the patient.

Hereinafter, discussion will be made on operational effects according to this embodiment.

In this embodiment, each medicine accommodating section 3 is formed to extend radially outward from the central section of medicine cartridge 7. Consequently, it is possible to locate medicine accommodating section 3 filled with the medicine for one dose, between medicine passage 31 and inflow passage 11 upon every rotation of medicine cartridge 7 by a certain peripheral angle.

Hereinafter, discussion will be made on technical ideas not claimed in claims and comprehended from the above embodiment.

(A) A medicine cartridge comprises a medicine accommodating body including a plurality of medicine accommodating sections formed side by side with each other in a peripheral direction of the medicine accommodating body. A section defining an inflow hole is formed at the inner peripheral side of the medicine accommodating body to supply air into the medicine accommodating section. Additionally, a section defining an outflow hole is formed at the outer peripheral side of the medicine accommodating body to flow out the medicine introduced by air. Here, the inflow hole and the outflow hole are located opposite to each other.

In this configuration, the inflow hole and the outflow hole are located opposite to each other, and therefore the patient who is weak in suction power can readily inhale medicine without remaining medicine within the medicine accommodating section.

(A-1) In a medicine cartridge as described in (A), the medicine accommodating body is formed annular.

In this configuration, the medicine accommodating body is formed annular and formed with the installation opening at the side of the inner periphery. Consequently, in case that the medicine cartridge is set to the cartridge accommodating section, the installation opening is fit with the cartridge accommodating section of the medicine administering apparatus to accomplish a secure keeping for the medicine cartridge. Additionally, a rotating mechanism for the medicine cartridge can be readily constituted when the medicine cartridge is installed to the cartridge accommodating section.

(A-2) In a medicine cartridge as described in (A) or (A-1), the medicine cartridge is formed into a trapezoid shape in cross-section.

In this configuration, the medicine cartridge is formed into the trapezoid shape in cross-section. Consequently, when the medicine cartridge is set in the cartridge accommodating section, clearance is never formed between the medicine cartridge and the fitting surface of the cartridge accommodating section so that the medicine cartridge can be securely retained by the cartridge accommodating section.

(A-3) In a medicine cartridge as described in any of (A) to (A-2), a tape-like member seals each of the inflow hole and the outflow hole in the medicine accommodating section.

In this configuration, the tape-like member seals each of the inflow hole and the outflow hole of the medicine accommodating section. Consequently, the inflow hole and the outflow hole can be opened upon readily forming a hole in the tape-like member so that an inhaling operation can be facilitated.

(A-4) In a medicine cartridge as described in any of (A) to (A-3), the medicine accommodating section is formed generally cylindrical.

In this configuration, the medicine can be effectively accommodated in the medicine accommodating section, and additionally the patient can inhale medicine into their rungs without remaining medicine within the medicine accommodating section.

(A-5) In a medicine cartridge as described in any of (A) to (A-4), the medicine cartridge is formed at its lower surface with depressions which are located corresponding to the respective medicine accommodating sections.

In this configuration, the position of the medicine cartridge in a peripheral direction can be securely retained when the medicine cartridge is rotated in the peripheral direction.

(A-6) In a medicine cartridge as described in (A-5), each of the depression is formed generally hemispherical.

In this configuration, the medicine cartridge can be smoothly rotated, and additionally the position of the medicine cartridge in the peripheral direction can be securely retained.

(B) A medicine cartridge comprises a medicine accommodating body including a plurality of medicine accommodating sections formed side by side with each other in a peripheral direction of the medicine accommodating body. A section defining an inflow hole is formed at the inner peripheral side of the medicine accommodating body to supply air into the medicine accommodating section. Additionally, a section defining an outflow hole is formed at the outer peripheral side of the medicine accommodating body to flow out the medicine introduced by air. Here, the introduction passage, the inflow hole, and the outflow hole are arranged along a generally straight line.

In this configuration, the introduction passage, the inflow hole, and the outflow hole are arranged in the generally straight line. Consequently, the patient who is weak in suction power can readily inhale medicine into his or her lungs without remaining medicine within the medicine accommodating section.

(B-1) In a medicine cartridge as described in (B), the medicine accommodating body is formed annular.

In this configuration, the medicine accommodating body is formed annular so that the installation opening is formed at the inner peripheral side. Consequently, in case that the medicine cartridge is set to the cartridge accommodating section, the installation opening is fit with the cartridge accommodating section of the medicine administering apparatus to accomplish a secure keeping for the medicine cartridge. Additionally, the rotating mechanism for the medicine cartridge can be readily constituted when the medicine cartridge is installed to the cartridge accommodating section.

(B-2) In a medicine cartridge as described in (B) or (B-1), a tape-like member seals each of the inflow hole and the outflow hole of the medicine accommodating section.

In this configuration, the tape-like member seals each of the inflow hole and the outflow hole of the medicine accommodating section. Consequently, the inflow hole and the outflow hole can be opened upon readily forming a hole in the tape-like member so that an inhaling operation can be facilitated.

(B-3) In a medicine cartridge as described in any of (B) to (B-2), the medicine cartridge is formed into a trapezoid shape in cross-section.

In this configuration, the medicine cartridge is formed into the trapezoid shape in cross-section. Consequently, when the medicine cartridge is set in the cartridge accommodating section, clearance is never formed between the medicine cartridge and the fitting surface of the cartridge accommodating section so that the medicine cartridge can be securely retained by the cartridge accommodating section.

(B-4) In a medicine cartridge as described in any of (B) to (B-3), the medicine accommodating section is formed generally cylindrical.

In this configuration, the medicine can be effectively accommodated in the medicine accommodating section, and additionally the patient can inhale medicine into their rungs without remaining medicine within the medicine accommodating section.

(B-5) In a medicine cartridge as described in any of (B) to (B-4), the medicine cartridge is formed at its lower surface with depressions which are located corresponding to the respective medicine accommodating sections.

In this configuration, the position of the medicine cartridge in a peripheral direction can be securely retained when the medicine cartridge is rotated in the peripheral direction.

(B-6) In a medicine cartridge as described in (B-5), each of the depression is formed generally hemispherical.

In this configuration, the medicine cartridge can be smoothly rotated, and additionally the position of the medicine cartridge in its peripheral direction can be securely retained.

(C) A medicine cartridge is used in an inhaling type medicine administering apparatus including a cartridge accommodating section, a section defining an inflow passage through which air is supplied, and a suction mouth. The medicine cartridge includes a medicine accommodating body having a plurality of medicine accommodating sections formed side by side with each other in a peripheral direction of the medicine accommodating body. A section defining an inflow hole is formed at the inner peripheral side of the medicine accommodating body to supply air into the medicine accommodating section. Additionally, a section defining an outflow hole is formed at the outer peripheral side of the medicine accommodating body to flow out the medicine introduced by air. Here, the inflow hole and the outflow hole are located opposite to each other.

In this configuration, the inflow hole and the outflow hole are located opposite to each other, and therefore the patient who is weak in suction power can readily inhale medicine into their lungs without remaining medicine within the medicine accommodating section.

(C-1) In a medicine cartridge as described in (C), an introduction passage is formed to be a part of the medicine accommodating section and provided at its one end side with the inflow hole and at its the other end side with the outflow hole. Here, the introduction passage, the inflow hole, and the outflow hole are arranged along a generally straight line in the medicine accommodating section.

In this configuration, the introduction passage, the inflow hole, and the outflow hole are arranged along the generally straight line. Consequently, the patient who is weak in suction power can readily inhale medicine into his or her lungs without remaining medicine within the medicine accommodating section.

(C-2) In a medicine cartridge as described in (C) or (C-1), the medicine cartridge is formed into a trapezoid shape in cross-section.

In this configuration, the medicine cartridge is formed into the trapezoid shape in cross-section. Consequently, when the medicine cartridge is set in the cartridge accommodating section, clearance is never formed between the medicine cartridge and the fitting surface of the cartridge accommodating section so that the medicine cartridge can be securely retained by the cartridge accommodating section.

(C-3) In a medicine cartridge as described in any of (C) to (C-2), a tape-like member seals each of the inflow hole and the outflow hole in the medicine accommodating section.

In this configuration, the tape-like member seals each of the inflow hole and the outflow hole of the medicine accommodating section. Consequently, the inflow hole and the outflow hole can be opened upon readily forming a hole in the tape-like member so that an inhaling operation can be facilitated.

(C-4) In a medicine cartridge as described in any of (C) to (C-3), the medicine accommodating section is formed generally cylindrical.

In this configuration, the medicine can be effectively accommodated in the medicine accommodating section, and additionally the patient can inhale medicine into their rungs without remaining medicine within the medicine accommodating section.

(C-5) In a medicine cartridge as described in any of (C) to (C-4), the medicine cartridge is formed at its lower surface with depressions which are located corresponding to the respective medicine accommodating sections.

In this configuration, the position of the medicine cartridge in a peripheral direction can be securely retained when the medicine cartridge is rotated in the peripheral direction.

(C-6) In a medicine cartridge as described in (C-5), each of the depression is formed generally hemispherical.

In this configuration, the medicine cartridge can be smoothly rotated, and additionally the position of the medicine cartridge in the peripheral direction can be securely retained.

(C-7) In a medicine cartridge as described in any of (C) to (C-6), a supporting means is provided for supporting the medicine cartridge to the cartridge accommodating section.

In this configuration, the position of the medicine cartridge in a peripheral direction can be securely kept when the medicine cartridge is rotated.

(C-8) In a medicine cartridge as described in (C-7), the supporting means includes a spherical supporting member and an elastic member.

In this configuration, the medicine cartridge is smoothly rotated, and additionally the position of the medicine cartridge in the peripheral direction can be elastically securely kept.

(C-9) In a medicine cartridge as described in any of (C) to (C-8), the cartridge accommodating section includes the pin accommodating section.

In this configuration, the pin accommodating section can be effectively arranged thereby making it possible to make the medicine administering apparatus compact in size.

(D) An inhaling type medicine administering apparatus comprises a medicine cartridge, a cartridge accommodating section, a section defining an inflow passage through which air is supplied, and a suction mouth. Here, the medicine cartridge includes a medicine accommodating body having a plurality of medicine accommodating sections formed side by side with each other in a peripheral direction of the medicine accommodating body. A section defining an inflow hole is formed at the inner peripheral side of the medicine accommodating body to supply air into the medicine accommodating section. Additionally, a section defining an outflow hole is formed at the outer peripheral side of the medicine accommodating body to flow out the medicine introduced by air. Here, the introduction passage, the inflow hole, and the outflow hole are arranged along a generally straight line in the medicine accommodating section.

In this configuration, the introduction passage, the inflow hole, and the outflow hole are arranged along the generally straight line. Consequently, the patient who is weak in suction power can readily inhale medicine into his or her lungs without remaining medicine within the medicine accommodating section.

(D-1) In an inhaling type medicine administering apparatus as described in (D), a tape-like member seals each of the inflow hole and the outflow hole of the medicine accommodating section.

In this configuration, the tape-like member seals each of the inflow hole and the outflow hole of the medicine accommodating section. Consequently, the inflow hole and the outflow hole can be opened upon readily forming a hole in the tape-like member so that an inhaling operation can be facilitated.

(D-2) In an inhaling type medicine administering apparatus as described in (D) or (D-1), the medicine cartridge is formed into a trapezoid shape in cross-section.

In this configuration, the medicine cartridge is formed into the trapezoid shape in cross-section. Consequently, when the medicine cartridge is set in the cartridge accommodating section, clearance is never formed between the medicine cartridge and the fitting surface of the cartridge accommodating section so that the medicine cartridge can be securely retained by the cartridge accommodating section.

(D-3) In an inhaling type medicine administering apparatus as described in any of (D) to (D-2), the medicine accommodating section is formed generally cylindrical.

In this configuration, the medicine can be effectively accommodated in the medicine accommodating section, and additionally the patient can inhale medicine into their rungs without remaining medicine within the medicine accommodating section.

(D-4) In an inhaling type medicine administering apparatus as described in any of (D) to (D-3), the medicine cartridge are formed at its lower surface with depressions which are located corresponding to the respective medicine accommodating sections.

In this configuration, the position of the medicine cartridge in a peripheral direction can be securely retained when the medicine cartridge is rotated in the peripheral direction.

(D-5) In an inhaling type medicine administering apparatus as described in (D-4), each of the depressions is formed generally hemispherical.

In this configuration, the medicine cartridge can be smoothly rotated, and additionally the position of the medicine cartridge in the peripheral direction can be securely retained.

(D-6) In an inhaling type medicine administering apparatus as described in any of (D) to (D-5), a supporting means is provided for supporting the medicine cartridge to the cartridge accommodating section.

In this configuration, the position of the medicine cartridge in a peripheral direction can be securely kept when the medicine cartridge is rotated.

(D-7) In an inhaling type medicine administering apparatus as described in (D-6), the supporting means includes a spherical supporting member and an elastic member.

In this configuration, the medicine cartridge is smoothly rotated, and additionally the position of the medicine cartridge in the peripheral direction can be elastically securely kept.

(D-8) In an inhaling type medicine administering apparatus as described in (D) to (D-7), the cartridge accommodating section includes the pin accommodating section.

In this configuration, the pin accommodating section can be effectively arranged thereby making it possible to make the medicine administering apparatus compact in size.

(E) A medicine cartridge is used in an inhaling type medicine administering apparatus comprises a cartridge accommodating section, a section defining an inflow passage through which air is supplied, and a suction mouth. Here, the medicine cartridge includes a medicine accommodating body having a plurality of medicine accommodating sections formed side by side with each other in a peripheral direction of the medicine accommodating body. A section defining an inflow hole is formed at the inner peripheral side of the medicine accommodating body to supply air into the medicine accommodating section. Additionally, a section defining an outflow hole is formed at the outer peripheral side of the medicine accommodating body to flow out the medicine introduced by air. Here, the medicine accommodating body is formed annular. The suction mouth is brought into communication with each of the medicine accommodating sections by rotating the medicine cartridge. The inflow hole and the outflow hole are located opposite to each other.

In this configuration, the inflow hole and the outflow hole are located opposite to each other, and therefore the patient who is weak in suction power can readily inhale medicine into their lungs without remaining medicine within the medicine accommodating section.

(E-1) In a medicine cartridge as described in (E), the introduction passage, the inflow hole, and the outflow hole are arranged along a generally straight line in the medicine accommodating section.

In this configuration, the introduction passage, the inflow hole, and the outflow hole are arranged along the generally straight line. Consequently, the patient who is weak in suction power can readily inhale medicine into his or her lungs without remaining medicine within the medicine accommodating section.

(E-2) In a medicine cartridge as described in (E) or (E-1), the medicine cartridge is formed into a trapezoid shape in cross-section.

In this configuration, the medicine cartridge is formed into the trapezoid shape in cross-section. Consequently, when the medicine cartridge is set in the cartridge accommodating section, clearance is never formed between the medicine cartridge and the fitting surface of the cartridge accommodating section so that the medicine cartridge can be securely retained by the cartridge accommodating section.

(E-3) In a medicine cartridge as described in (E) to (E-2), a tape-like member seals each of the inflow hole and the outflow hole of the medicine accommodating section.

In this configuration, the tape-like member seals each of the inflow hole and the outflow hole of the medicine accommodating section. Consequently, the inflow hole and the outflow hole can be opened upon readily forming a hole in the tape-like member so that an inhaling operation can be facilitated.

(E-4) In a medicine cartridge as described in any of (E) to (E-3), the medicine accommodating section is formed generally cylindrical.

In this configuration, the medicine can be effectively accommodated in the medicine accommodating section, and additionally the patient can inhale medicine into their rungs without remaining medicine within the medicine accommodating section.

(E-5) In a medicine cartridge as described in any of (E) to (E-4), the medicine cartridge is formed at its lower surface with depressions which are located corresponding to the respective medicine accommodating sections.

In this configuration, the position of the medicine cartridge in a peripheral direction can be securely retained when the medicine cartridge is rotated in the peripheral direction.

(E-6) In a medicine cartridge as described in (E-5), each of the depression is formed generally hemispherical.

In this configuration, the medicine cartridge can be smoothly rotated, and additionally the position of the medicine cartridge in the peripheral direction can be securely retained.

(E-7) In a medicine cartridge as described in any of (E) to (E-6), a supporting means is provided for supporting the medicine cartridge to the cartridge accommodating section.

In this configuration, the position of the medicine cartridge in a peripheral direction can be securely kept when the medicine cartridge is rotated.

(E-8) In a medicine cartridge as described in (E-7), the supporting means includes a spherical supporting member and an elastic member.

In this configuration, the medicine cartridge is smoothly rotated, and additionally the position of the medicine cartridge in the peripheral direction can be elastically securely kept.

(E-9) In a medicine cartridge as described in (E) to (E-8), the cartridge accommodating section includes the pin accommodating section.

In this configuration, the pin accommodating section can be effectively arranged thereby making it possible to make the medicine administering apparatus compact in size.

(F) An inhaling type medicine administering apparatus comprises a medicine cartridge, a cartridge accommodating section, a section defining an inflow passage through which air is supplied, and a suction mouth. Here, the medicine cartridge includes a medicine accommodating body having a plurality of medicine accommodating sections formed side by side with each other in a peripheral direction of the medicine accommodating body. A section defining an inflow hole is formed at the inner peripheral side of the medicine accommodating body to supply air into the medicine accommodating section. Additionally, a section defining an outflow hole is formed at the outer peripheral side of the medicine accommodating body to flow out the medicine introduced by air. Here, the medicine accommodating body is formed annular. The suction mouth is brought into communication with each of the medicine accommodating sections by rotating the medicine cartridge. The introduction passage, the inflow hole, and the outflow hole are arranged along a generally straight line in the medicine accommodating section.

In this configuration, the introduction passage, the inflow hole, and the outflow hole are arranged along the generally straight line. Consequently, the patient who is weak in suction power can readily inhale medicine into his or her lungs without remaining medicine within the medicine accommodating section.

(F-1) In an inhaling type medicine administering apparatus as described in (F), a tape-like member seals each of the inflow hole and the outflow hole of the medicine accommodating section.

In this configuration, the tape-like member seals each of the inflow hole and the outflow hole of the medicine accommodating section. Consequently, the inflow hole and the outflow hole can be opened upon readily forming a hole in the tape-like member so that an inhaling operation can be facilitated.

(F-2) In an inhaling type medicine administering apparatus as described in (F) or (F-1), the medicine cartridge is formed into a trapezoid shape in cross-section.

In this configuration, the medicine cartridge is formed into the trapezoid shape in cross-section. Consequently, when the medicine cartridge is set in the cartridge accommodating section, clearance is never formed between the medicine cartridge and the fitting surface of the cartridge accommodating section so that the medicine cartridge can be securely retained by the cartridge accommodating section.

(F-3) In an inhaling type medicine administering apparatus as described in any of (F) to (F-2), the medicine accommodating section is formed generally cylindrical.

In this configuration, the medicine can be effectively accommodated in the medicine accommodating section, and additionally the patient can inhale medicine into their rungs without remaining medicine within the medicine accommodating section.

(F-4) In an inhaling type medicine administering apparatus as described in any of (F) to (F-3), the medicine cartridge is formed at its lower surface with depressions which are located corresponding to the respective medicine accommodating sections.

In this configuration, the position of the medicine cartridge in a peripheral direction can be securely retained when the medicine cartridge is rotated in the peripheral direction.

(F-5) In an inhaling type medicine administering apparatus as described in (F-4), each of the depression is formed generally hemispherical.

In this configuration, the medicine cartridge can be smoothly rotated, and additionally the position of the medicine cartridge in the peripheral direction can be securely retained.

(F-6) In an inhaling type medicine administering apparatus as described in any of (F) to (F-5), a supporting means is provided for supporting the medicine cartridge to the cartridge accommodating section.

In this configuration, the position of the medicine cartridge in a peripheral direction can be securely kept when the medicine cartridge is rotated.

(F-7) In an inhaling type medicine administering apparatus as described in (F-6), the supporting means includes a spherical supporting member and an elastic member.

In this configuration, the medicine cartridge is smoothly rotated, and additionally the position of the medicine cartridge in the peripheral direction can be elastically securely kept.

(F-8) In an inhaling type medicine administering apparatus as described in (F) to (F-7), the cartridge accommodating section includes the pin accommodating section.

In this configuration, the pin accommodating section can be effectively arranged thereby making it possible to make the medicine administering apparatus compact in size.

In this embodiment, discussion has been made on the medicine administering apparatus of the type wherein the medicine is inhaled through the oral cavity. However, the invention is not limited to the embodiment described above. Modification and variation of the embodiment described above will occur to those skilled in the art, in light of the above teachings. For example, the invention is applicable to the medicine administering apparatus of the type wherein the medicine is inhaled through a nasal cavity.

The entire contents of Japanese Patent Application No. 2004-323910, filed Nov. 8, 2004, is incorporated herein by reference.

What is claimed is:

1. A medicine cartridge comprising:
   a rotatable annular medicine accommodating body including a plurality of medicine accommodating sections formed side by side with each other in a peripheral direction of said medicine accommodating body, said medicine accommodating body having an inner peripheral surface and an outer peripheral surface which are coaxial with each other, each medicine accommodating section accommodating therein medicine in powder form and radially extending from the inner peripheral surface to the outer peripheral surface of said medicine accommodating body;
   a section defining an inflow hole formed at one end of the medicine accommodating section and located at the inner peripheral surface of said medicine accommodating body to supply air into the medicine accommodating section; and
   a section defining an outflow hole formed at the other end of the medicine accommodating section and located at the outer peripheral surface of said medicine accommodating body to flow out the medicine introduced by air.

2. An inhaling type medicine administering apparatus comprising:
   a medicine cartridge;
   a cartridge accommodating section for detachably accommodating said medicine cartridge;
   a section defining an inflow passage through which air is supplied into a medicine accommodating section of said medicine cartridge; and
   a suction mouth through which the medicine in the medicine accommodating section is drawn out with air supplied from the inflow passage and administered into lungs of a person,
   wherein said medicine cartridge includes a rotatable annular medicine accommodating body including a plurality of medicine accommodating sections formed side by side with each other in a peripheral direction of the medicine accommodating body, the medicine accommodating body having an inner peripheral surface and an outer peripheral surface which are coaxial with each other, each medicine accommodating section accommodating therein medicine in powder form and radially extending from the inner peripheral surface to the outer peripheral surface of the medicine accommodating body; a section defining an inflow hole formed at one end of the medicine accommodating section and located at the inner peripheral surface of the medicine accommodating body to supply air into the medicine accommodating section; and a section defining an outflow hole formed at the other end of the medicine accommodating section and located at the outer peripheral surface of the medicine accommodating body to flow out the medicine introduced by air.

3. An inhaling type medicine administering apparatus comprising:
   a medicine cartridge;

a cartridge accommodating section for detachably accommodating said medicine cartridge;
a section defining an inflow passage through which air is supplied into a medicine accommodating section of said medicine cartridge; and
a suction mouth through which the medicine in the medicine accommodating section is drawn out with air supplied from the inflow passage and administered into lungs of a person,
wherein said medicine cartridge includes a rotatable annular medicine accommodating body including a plurality of medicine accommodating sections formed side by side with each other in a peripheral direction of the medicine accommodating body, the medicine accommodating body having an inner peripheral surface and an outer peripheral surface which are coaxial with each other, each medicine accommodating section accommodating therein medicine in powder form and radially extending from the inner peripheral surface to the outer peripheral surface of the medicine accommodating body; a section defining an inflow hole formed at one end of the medicine accommodating section and located at the inner peripheral surface of the medicine accommodating body to supply air into the medicine accommodating section; and a section defining an outflow hole formed at the other end of the medicine accommodating section and located at the outer peripheral surface of the medicine accommodating body to flow out the medicine introduced by air,
wherein said suction mouth is brought into communication with each of the medicine accommodating sections by rotating the medicine cartridge.

* * * * *